United States Patent
Ban et al.

(10) Patent No.: US 8,195,283 B2
(45) Date of Patent: Jun. 5, 2012

(54) PET BODY FAT MEASURING TOOL

(75) Inventors: Takeshi Ban, Tokyo (JP); Masayuki Okawa, Tokyo (JP); Tomoshige Umeda, Tokyo (JP); Kazuya Otsuji, Tokyo (JP)

(73) Assignee: Kao Corporation, Tokyo (JP)

( * ) Notice: Subject to any disclaimer, the term of this patent is extended or adjusted under 35 U.S.C. 154(b) by 569 days.

(21) Appl. No.: 11/909,661

(22) PCT Filed: Mar. 17, 2006

(86) PCT No.: PCT/JP2006/305385
§ 371 (c)(1), (2), (4) Date: Mar. 13, 2008

(87) PCT Pub. No.: WO2006/103958
PCT Pub. Date: Oct. 5, 2006

(65) Prior Publication Data
US 2009/0076408 A1    Mar. 19, 2009

(30) Foreign Application Priority Data

Mar. 25, 2005 (JP) .................................. 2005-88100
Dec. 27, 2005 (JP) ................................ 2005-373972

(51) Int. Cl.
*A61B 5/05* (2006.01)
*A61B 5/04* (2006.01)

(52) U.S. Cl. ....................................... 600/547; 600/393

(58) Field of Classification Search .................. 600/393, 600/547
See application file for complete search history.

(56) References Cited

U.S. PATENT DOCUMENTS

| | | | | |
|---|---|---|---|---|
| 5,823,957 A | * | 10/1998 | Faupel et al. | 600/397 |
| 5,964,703 A | * | 10/1999 | Goodman et al. | 600/547 |
| 6,129,666 A | * | 10/2000 | DeLuca et al. | 600/393 |
| 7,184,822 B2 | * | 2/2007 | Kasahara et al. | 600/547 |
| 2001/0030546 A1 | | 10/2001 | Yamada et al. | |
| 2004/0167386 A1 | | 8/2004 | Kasahara et al. | |

(Continued)

FOREIGN PATENT DOCUMENTS

EP    1 138 259 A2    10/2001

(Continued)

OTHER PUBLICATIONS

Murata, Machine Translation of JP 2002-253523 A, pp. 1-9.*

(Continued)

*Primary Examiner* — Max Hindenburg
*Assistant Examiner* — Emily Lloyd
(74) *Attorney, Agent, or Firm* — Oblon, Spivak, McClelland, Maier & Neustadt, L.L.P.

(57) ABSTRACT

A pet body fat measuring tool and method for measuring pet body fat by measuring a bioelectrical impedance includes an electrode body including at least two current electrodes and at least two voltage electrodes. The electrode body is pressed to a part of a pet body. The tool also includes a control calculating unit having an impedance measuring circuit connected to the electrode body to control a current made to flow at a time of measurement. The control calculating unit includes, in advance of the measurement, a direct correlation between a body fat percentage of a pet body and the bioelectrical impedance of the pet body to calculate the body fat percentage based on only a bioelectrical impedance determined from measured voltages. A distance between each of the current electrodes and each of the voltage electrode is fixed.

15 Claims, 6 Drawing Sheets

U.S. PATENT DOCUMENTS

2008/0167536 A1 * 7/2008 Teller et al. .................. 600/301

FOREIGN PATENT DOCUMENTS

| EP | 1 452 132 A2 | 9/2004 |
| JP | 2001-299717 | 10/2001 |
| JP | 2002-253523 | 9/2002 |
| JP | 2002-253523 A * | 9/2002 |
| JP | 2002-369806 | 12/2002 |
| JP | 2003-144005 | 5/2003 |
| JP | 2004-254616 | 9/2004 |
| JP | 2005-27661 | 2/2005 |
| WO | WO 2004/032715 A2 | 4/2004 |
| WO | WO 2004/112605 A1 | 12/2004 |

OTHER PUBLICATIONS

Office Action issued Dec. 6, 2011, in Japanese Patent Application No. 2009-152258 with English translation.

European Communication pursuant to Article 94(3) EPC issued Nov. 9, 2010, in Application No. 06 729 375.3-1265.

* cited by examiner

<③ Electrodes arranged in square shape>

<② Electrodes arranged in straight line, vertical to median line>

<① Electrodes arranged in straight line, parallel to median line>

PET BODY FAT MEASURING TOOL

CROSS REFERENCE TO RELATED APPLICATIONS

The present application is a national stage application of PCT/JP06/305385, which was filed on Mar. 17, 2006, and which claims priority to Japanese Application No. 2005-088100, which was filed on Mar. 25, 2005, and Japanese Application No. 2005-373972, which was filed on Dec. 27, 2005.

TECHNICAL FIELD

The present invention relates to a pet body fat measuring tool and a pet body fat measuring method, and more particularly to the pet body fat measuring tool and pet body fat measuring method which are capable of measuring body fat of a small-sized animal raised as a pet such as a dog, cat, or the like by measuring and calculating bioelectrical impedance.

BACKGROUND TECHNOLOGY

Obesity caused by the abundance of food in recent years presents a problem. It has been recognized that obesity is a big factor to life-habit diseases such as heart disease, arterial sclerosis, hypertension, diabetes, or the like and, therefore, management of accumulated amounts of fat in the body is important to keep and improve one's daily health, which induces development of various body fat meters. As such a body fat meter, a body fat measuring device fabricated according to an impedance method to measure a bioelectrical impedance is known (Japanese Patent Publication No. 2002-369806).

On the other hand, a dog, cat, or the like being a small-sized animal raised as a pet have also an abundance of food and, there are many cases in which, for example, a pet owner feeling a sense of attachment to a pet wishes to properly manage pet body fat and to control feeding amounts so that these pets do not become fat and to maintain and improve the health of its dog, cat, or the like. Also, an impedance measuring tool is disclosed in which the measuring method of body fat according to the impedance method which has been applied to a human body is applied to domestic animals (Japanese Patent Publication No. 2002-253523). Furthermore, by having the problem that pet body hairs constitute an electrical insulator, some related technologies are disclosed in order to increase measuring accuracy which include technology to improve the shape of an electrode being in contact with a pet body (see Japanese Patent Publication No. 2003-144005), technology to make an electrolysis solution be held and supported between a contact region of a pet and an electrode (Japanese Patent Publication No. 2005-27661), and technology to use a measuring tool so that an electrode is in touch only with a root of limbs having little body hairs (Japanese Patent Publication No. 2004-254616).

DISCLOSURE OF THE INVENTION

The present invention provides a pet body fat measuring tool for measuring pet body fat by measuring and calculating bioelectrical impedance, which includes an electrode body having at least two voltage electrodes and at least two current electrodes and being used by being pressed to a part of a pet body and a control calculating unit having an impedance measuring circuit connected to the electrode body to control a current made to flow at a time of measurement and to calculate body fat based on the bioelectrical impedance determined from measured voltages, wherein a distance between each of the voltage electrodes and each of the current electrodes of the electrode body and a distance between the voltage electrodes of the electrode body are fixed. Moreover, the present invention also provides a pet body fat measuring method to measure and calculate bioelectric impedance by using the above pet body fat measuring tool to measure pet body fat.

DETAILED DESCRIPTION OF THE INVENTION

Figure 1:
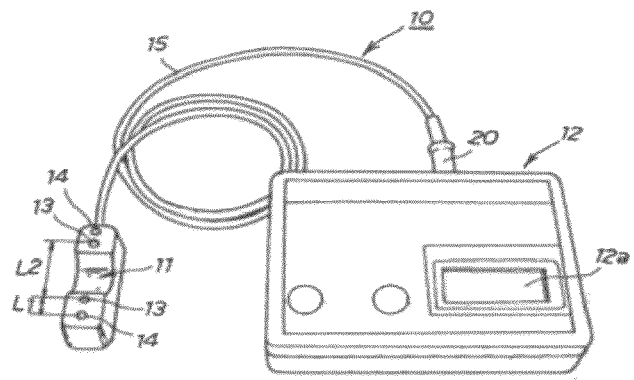
FIG. 1 is a perspective view explaining a pet body fat measuring tool according to an embodiment of the present invention.

A body fat meter using a bioelectrical impedance method is configured so that, based on facts that a conductive property of water in body is good and, therefore, if a water content in body is high, a current is easy to flow and electric resistance decreases, while, a water content contained in body fat is low and a conductive property of a body fat tissue is bad and, therefore, an electric resistance increases in a human having much body fat, body fat is measured by measuring bioelectrical impedance by making a current of a low level flow through a human's body to estimate a water content and a fat-free amount. However, when this method is applied, in order to improve its measuring accuracy, data on body weight, body length, girth, or the like is required, which makes its method slightly complicated as a result.

On the other hand, there is a report that a correlation between thickness of fat in the ribs of a female beagle and a body fat percentage is seen (Anderson, D. B., Corbin, J. E.: Estimating body fat in mature beagle bitches. Lab. Anim. Sci., 32: 367-370). Moreover, to measure the thickness of subcutaneous fatness in an abdomen, technology of measuring impedance of the abdomen is available (Scharfetter, H. Schalager, T. Stollbergr, R. Felsberger, R. Hutten, H. Hinghofer-Szalkay, H.: Assessing abdominal fatness with local bio-impedance analysis: basics and experimental findings. Int. J. Obesity., 25:502-511 (2001)) and, therefore, the application of the above impedance method to the ribs of a pet was envisioned. However, it can be readily analogized that, even if an absolute value of thickness of subcutaneous fat is simply the same, a body fat percentage differs at the case that each pet's physical status differs greatly. That is, the above impedance method is effective if the physical status of each pet to be measured is within a specified range; however, each physical status differs greatly in every individual pet and, therefore, it is judged that the above method cannot be applied when various pets being different in terms of physical status need to be measured.

An object of the present invention is to provide a pet body fat measuring tool and a pet body measuring method which are capable of easily and accurately measuring body fat of a small-sized animal raised as a pet such as a dog, cat, or the like by an impedance method without requiring much time and labor. To achieve this, inventors of the present invention have found as a result of research and study of an effective method of measuring pet body fat that, when electrodes arranged so as to have a fixed distance between the electrodes are used, there is a high correlation between the measured impedance and body fat percentage, irrespective of the physical status of an individual pet.

The term "body fat" used in the description of the pet body fat measuring method of the prevent invention, unless otherwise indicated clearly, is a concept that contains both the "body fat percentage" and "amount of body fat (weight, volume)".

In the pet body fat measuring tool of the present invention, the electrode body requires at least two current electrodes and at least two voltage electrodes, however, more accurate measurement is made possible by using three or more current electrodes and voltage electrodes to measure impedance among the electrodes. Materials for the electrodes need to be electrically conductive and, therefore, metal such as copper, iron, aluminum, brass, stainless steel, or a like can be used; however, from a viewpoint of being hard to rust, the use of stainless steel is preferable.

The shape of each of the electrodes may be circular, cylindrical, plate-like, convex and so on, and can be changed as appropriate depending on the region to which an electrode is to be applied. Preferably, the shape of the electrode when being sandwiched between axillary regions or inguinal regions is cylindrical and, when being pressed to a region where many body hairs grow, is convex. According to the present invention, it is necessary that the distance among electrodes is fixed and, therefore, it is preferable that a convex electrode is used to be pressed to regions except for the axillary and inguinal regions. Moreover, the size of each of the electrodes can be adjusted, as appropriate, depending on the size of a pet body or on a region to which the electrode is to be applied. In the case of a dog or cat, if the electrode is cylindrical, the electrode has preferably an outer diameter of about 5 mm to 20 mm, with its inner diameter being about 3 mm to 18 mm, and its length being about 5 mm to 30 mm, and if the electrode is convex, the electrode has preferably an outer diameter of about 2 mm to 30 mm, more preferably about 3 mm to 10 mm, with its height being 2 mm to 15 mm and more preferably about 3 mm to 10 mm. It is not necessary that the size of the voltage electrodes and current electrodes are the same. Additionally, it is preferable that the convex electrode is of a shape made up of a simple smooth convex face such as a surface of a sphere or a spindle since it can reduce pain in a pet.

It is necessary that, in the pet body fat measuring tool of the present invention, the distance between each of the voltage electrodes of the electrode body and each of the current electrodes of the electrode body and the distance between the voltage electrodes of the electrode body are fixed. The reason for that is, any change in the above distances causes a variation in measured values of impedances even in the same individual pet. To put it concretely, an example of the pet body fat measuring tool is shown in FIG. 1. Body fat (body fat percentage and amount of body fat) is calculated by a control calculating unit 12 having an impedance measuring circuit to control a current made to flow when the electrode body 11 of the pet body fat measuring tool 10 is pressed to a part of a pet body at a time of measurement and to calculate body fat based on the bioelectrical impedance determined from measured voltages. A region to which the electrode body 11 is to be pressed is preferably within a range of a half on a rear side of a body seen from a body side between the shoulder bone of the pet body and the iliac bone of the pet body by such reasons that the measurement is made easily even in a moving pet and that there is a high correlation between an impedance value and a body fat percentage in the region (see FIGS. 5[a] to 5[e]).

Figure 2:
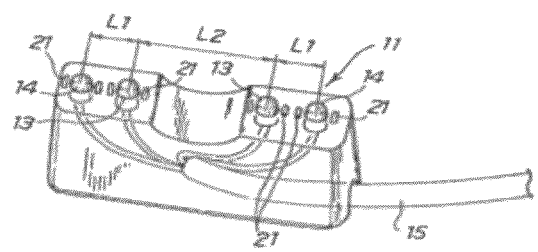
FIG. 2 is a perspective view showing one example of an electrode body of the pet body fat measuring tool according to an embodiment of the present invention.

The distance L1 between the center of each of the voltage electrodes 13 of the electrode body and the center of each of the current electrodes 14 of the electrode body, as shown in FIG. 2, is 5 mm to 30 mm, preferably 6 mm to 20 mm, and more preferably 8 mm to 15 mm, and the distance L2 between centers of the voltage electrodes 13 is 10 mm to 300 mm, preferably 10 mm to 200 mm, more preferably 15 mm to 100 mm, and even more preferably 20 mm to 60 mm, from a viewpoint that there is a high correlation between an impedance value and a body fat percentage. It is also preferable that each of the voltage electrodes 13 is separated from each of the current electrodes 14 by an insulator. As the insulator, rubber, plastics, wood, or the like are preferably used.

Figure 3:
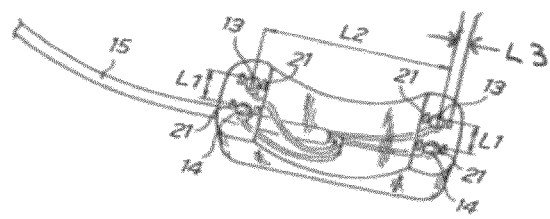
FIG. 3 is a perspective view showing one example of an electrode body according to another embodiment of the present invention.

Moreover, as shown in FIG. 1, to each of the current electrode 14 and voltage electrode 13 of the electrode body 11 is connected a connecting code 15 extending from the control calculating unit 12. By an instruction from the control calculating unit, a current is made to flow between the two current electrodes 14 of the electrode body 11 and a voltage between the two voltage electrodes 13 of the electrode body 11 is measured. Additionally, the current electrodes 14 and voltage electrodes 13 of the electrode body 11 may be arranged not only in a straight line as shown in FIGS. 1 and 2 but also in a manner to form, for example, a rectangular shape in two rows as shown in FIG. 3.

The control calculating unit 12 making up the pet body fat measuring tool 10 of the present invention includes a known control mechanism such as a micro-computer or the like and a known impedance measuring circuit, and is connected to the current electrodes 14 and voltage electrodes 13, thereby controlling a current made to flow at a time of the measurement. Also, a body fat percentage is calculated based on a bioelectrical impedance determined from measured voltages and the calculated body fat percentage is accumulated as measured data, both of which are allowed to be displayed on a displaying section 12a. Moreover, by inputting data on a body weight separately, a body fat amount (weight) can be displayed as well.

That is, the control calculating unit 12 controls so that a current of 0.1 mA to 1 mA flows for 0.02 seconds to 1.28 seconds between a pair of the current electrodes 14 one to ten times at intervals of 0.1 seconds to 5 seconds, for example, and that an average voltage can be calculated by using voltages between the voltage electrodes 13 as measured voltages. Also, in the impedance measuring circuit of the control calculating unit 12, data on the correlation between measured voltages and bioelectrical impedances or body fat percentages is input in advance and based on the bioelectrical impedance determined from measured voltages, a body fat percentage can be easily calculated, and a body fat amount (weight) also can be easily calculated by multiplying data on the body fat percentage to data on a weight which is separately input. The pet body fat measuring tool 10 of the present invention can be applied to any kind or size of a pet; however, in some cases, it can be configured so that, by inputting initial data on kind, sex, weight, or the like of a pet whose body fat is to be measured by the control calculating unit 12, data showing a correlation properly corresponding to pet kinds or the like can be selected by the impedance measuring circuit to enable more accurate calculation of body fat.

Moreover, the control calculating unit having the impedance measuring circuit may be used as a single and exclusive unit for a pet; however, it can be used, by switching, as a pet body fat measuring tool so that body fat of a pet is displayed on the displaying section by imbedding the above control calculating unit into a human body fat measuring tool and connecting a connecting code extending from the electrodes to the control calculating unit.

When pet body fat is measured by using the pet body fat measuring tool 10, if the pet gets dirty, fat on the skin is preferably removed in advance. To achieve this, the surface of the skin on which the electrode body 11 is pressed is wiped clean with a sponge, woven fabric, non-woven fabric, absorbent cotton, or the like impregnated with an organic solvent or surfactant. As the organic solvent, for example, a water soluble solvent such as ethanol, isopropyl alcohol, or the like can be used. As the organic solvent, one or more organic solvents may be used and an aqueous solution containing 10% to 100% by weight of an organic solvent can be preferably used and an aqueous solution containing 50% to 100% by weight of the organic solvent can be used more preferably. As the surfactant, an anion surfactant such as alkyl sulfate, polyoxyethylene alkylether sulfate, or the like, and an amphoteric surfactant such as alkyldimethyl aminoacetic acid betaine, alkylcalboxy methylhydroxy ethyl imidazolium betaine, alkylamidopropyl betaine, or the like can be used. It is preferable that, as a surfactant providing high veterinary and medical safety, a nonionic surfactant, in particular, including a fatty acid ester nonionic surfactant, polyoxyalkylene nonionic surfactant, alkylalkanol amido nonionic surfactant, or alkylglycoside nonionic surfactant is used. A solution, if being of a wash-away type such as shampoo, containing 10% to 25% by weight and, preferably, 15% to 20% by weight of one or more surfactants in a composition is used. A solution, if being of a no wash-away type, containing 0.1% to 5% by weight and, preferably, 0.5% to 2% by weight of one or more surfactants in a composition is used. Also, fat on the skin may be removed by wiping after dusting fat absorbing powder or wiping using woven fabrics made up of very slender fibers.

Moreover, the pet body fat measuring tool 10 of the present invention is used preferably in a manner in which, with each of the electrodes 13, 14 of the electrode body 11 being pressed to a part of a pet body, an electrolysis solution is held and supported between the electrodes 13, 14 and the surface of the pet body. This enables accurate measurement of body fat even if hairs as an insulator exist between the surface of the pet body and the electrodes 13, 14. As the electrolysis solution to be held and supported, for example, calcium chloride, sodium chloride, potassium chloride, or the like can be used. It is preferred that the concentration of a solute in these electrolysis solutions is 0.03% to 10%, preferably 0.2% to 10%, more preferably 0.5% to 5%. Too low concentration causes degradation of electrical conductive property, whereas too high concentration causes a sticky state after dried. It is preferred that an amount of each of these electrolysis solutions is about 0.1 cc to 10 cc per each of the electrodes 13, 14, preferably 1 cc to 5 cc, more preferably 2 cc to 4 cc. Too small amounts of the electrolysis solution cause a decreased conductive property and too large amounts of the electrolysis solution cause an uneconomical state and dripping into the surrounding area and, as a result, a floor or the like gets dirty. In order to increase adhesiveness of the electrolysis solution to a pet body, a thickener is used to raise viscosity of the electrolysis solution. As the thickener, a food additive such as acrylic acid polymer, CMC (CalboxyMethyl Cellulose), pectin, xanthangum, or the like can be used. From a viewpoint that a pet may lick the thickener, a food additive is preferably used. The viscosity of the electrolysis solution is within a range of 1 cps to 120,000 cps and can be changed, as necessary, depending on conditions such as the amount of hair of a pet and preferably 1 cps to 40 cps, more preferably 1 cps to 20 cps, which allows the electrolysis solution to be well infiltrated therein and can improve electrical conductivity even when body hairs exist between the electrodes 13, 14 and the surface of a pet body, enabling more accurate measurements. Moreover, it is preferable that, by the combined use of the organic solvent or surfactant to remove the fat on the skin and the electrolysis solution, both the removal of the fat on the skin and provision of the electrolysis solution can be achieved at the same time.

The pet body fat measuring tool 10 of the present invention is preferably used, from a viewpoint of measuring accuracy, by holding and supporting an organic solvent not containing an electrolyte, instead of the above electrolysis solution, between the surface of a pet body and electrode body. As the organic solvent to be held and supported, water-soluble organic solvent such as ethanol, isopropylalcohol, or the like is used preferably. It is preferred that the solution containing 10% to 100% by weight and preferably 50% to 100% by weight of a mixture of one or more organic solvents is used from a viewpoint of measuring accuracy.

Moreover, by sandwiching an electrolysis solution or organic solvent impregnating body made up of a sponge, woven fabric, unwoven fabric, absorbent cotton, or the like being impregnated with these electrolysis solutions or organic solvents between each of the electrodes 13, 14 and the surface of a pet body, body hairs between each of the electrodes 13, 14 and a surface of a pet body are made to support the electrolysis solutions or organic solvents.

Figure 4A:
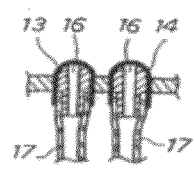
FIG. 4(a) is a partial cross-sectional view showing configurations of the pet body fat measuring tool in which an electrolysis solution or organic solvent is directly supplied to a surface of each electrode from an electrolysis solution or organic solvent supplying section directly connected to each electrode.
Figure 4B:
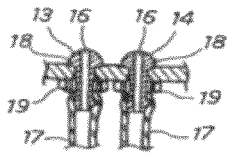
FIG. 4(b) is a partial cross-sectional view showing configurations of the pet body fat measuring tool in which an electrolysis solution or organic solvent is directly supplied to a surface of each electrode from the electrolysis solution or organic solvent supplying section directly connected to each electrode.

The above electrolysis solution or organic solvent is preferably supplied by an electrolysis solution or organic solvent supplying section directly connected to a surface of each of the electrodes 13, 14, to the surface of the electrode body 11. More specifically, for example as shown in FIGS. 4(a) and 4(b), each of the electrodes 13, 14 is configured so that the electrolysis solution or organic solution is supplied to the surface of each of the electrodes 13, 14 being in direct contact with a pet, by forming a hole 16 in each of central portions of the electrodes 13, 14 and by connecting each of the electrolysis solution or organic solvent supplying tubes 17 to an opposite side of each surface of the electrodes 13, 14 being in direct touch with a pet body to allow the electrolysis solution or organic solvent to be emitted. As materials for the electrodes 13, 14 in this case, for example, platinum, gold, silver, silver chloride, copper, aluminum, stainless steel, resin plated with metal, or the like can be used. In this case, a diameter of the hole 16, if being a circular hole, may be preferably 1 mm to 5 mm, more preferably 1.2 mm to 3 mm.

As materials for the electrolysis solution or organic solvent supplying tubes 17, for example, general materials such as nylon, silicone rubber, vinyl resin, or the like can be employed without any restraint. The tubes 17 may be attached so as to correspond to each of the electrodes 13, 14 or so as to be combined into, for example, two pieces of the tubes or one piece of the tube. The electrolysis solution or organic solvent supplying section may be configured so that an electrolysis solution or organic solution is supplied by pressing, whenever necessary, for example, a syringe-shaped solution trap in which the electrolysis solution or organic solvent is held and supported or by using a syringe, washing bottle, manual pump, electrical pump, or the like and the electrolysis solution or organic solvent can be fed manually or electrically. Moreover, a sponge-like holding body may be attached to a tip of the electrolysis solution or organic solvent supplying section and an electrode plate may be formed on a surface of the sponge-like holding body. An amount of the electrolysis solution or organic solvent to be supplied from the above supplying section is preferably, for example, 4 cc to 20 cc a time. An amount of the electrolysis solution or organic solvent to be emitted from the electrodes 13, 14 is 1 cc to 3 cc, for example, in the case of a short-hair species of dog for every one electrode out of electrodes 13, 14 and 2 cc to 5 cc in the case of a long-hair species of dog for every one electrode out of electrodes 13, 14.

Figure 10:
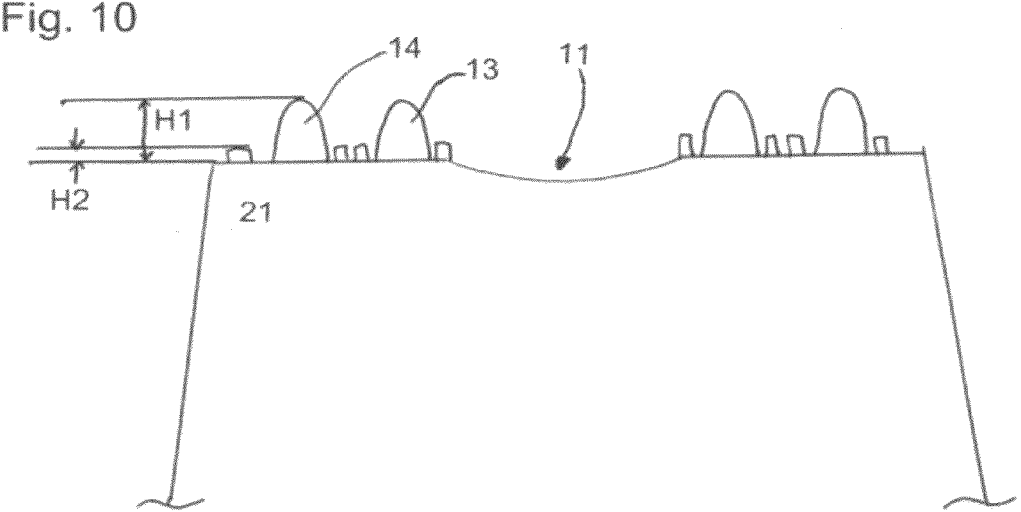
FIG. 10 is an enlarged side view showing a portion of one example of an electrode body of the pet body fat measuring tool according to an embodiment of the present invention.
Figure 11:
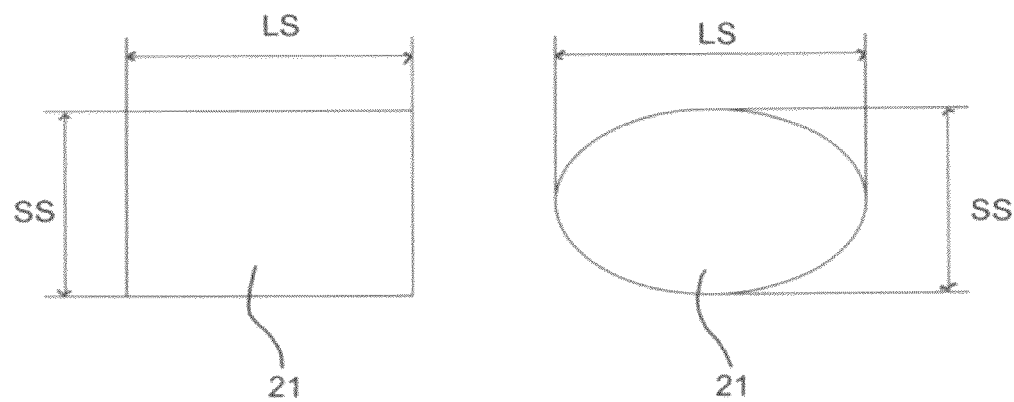
FIG. 11 is a cross-sectional top view showing exemplary protrusions of one example of an electrode body of the pet body fat measuring tool according to an embodiment of the present invention.

As shown in FIGS. 2 and 3, it is preferred that one or more protrusions 21 are placed in a portion surrounding each of the electrodes 13, 14 with an interval (L3 in FIG. 3) of 0.5 mm to 10 mm, preferably 0.8 to 5 mm, more preferably 1 mm to 2 mm from an outer region of each of the electrodes 13, 14 from a viewpoint of easiness of pushing the body hair aside when the electrode body 11 is pressed to a pet with much body hair and of easiness of bringing the electrodes 13, 14 in close contact with the surface of a pet body. When two or more protrusions 21 are arranged, these protrusions are each formed in an individual and separate manner. As shown in FIG. 10, it is preferred that the height H1 of each of the protrusions 21 is lower than the height H2 of each of the electrodes 13, 14 and a difference (H1−H2) between the height of each of the protrusions 21 and each of the electrodes 13, 14 is within 5 mm, preferably within 3 mm, more preferably within 2 mm from a viewpoint from easiness of pushing body hairs aside and of bringing the electrodes 13, 14 in close touch with the surface of a pet body. The number of the protrusions 21 is preferably 1 piece to 4 pieces per one electrode and more preferably 2 pieces from a viewpoint of easiness of bringing the electrodes 13, 14 in close touch with the surface of a pet body. As shown in FIG. 11, the cross section of each of the protrusions 21 may be elliptic or rectangular with its long side LS being 1 mm to 5 mm, preferably 2 mm to 4 mm and with its short side SS being 1 mm to 3 mm, preferably 2 mm to 3 mm and may be triangular with its one side being 1 mm to 5 mm, preferably 2 mm to 4 mm and may be circular with its diameter being 1 mm to 5 mm, preferably 2 mm to 4 mm, or may be of any shape obtained by combining these shapes. Moreover, it is preferred that each of the protrusions 21 is arranged so that a line connecting the center of each of the electrodes 13, 14 with the center of each of the protrusion 21 placed in portions surrounding the electrodes 13, 14 is vertical to a flowing direction of pet body hairs from a viewpoint that pet hairs can be pushed aside with an easy operation. Generally, pet body hairs grow in the direction from the head toward the tail and, therefore, when the protrusions 21 are arranged in the same line in which the electrodes 13, 14 of the electrode body 11 are arranged in a straight line, preferably, the measurement is made with the electrode body 11 being pressed in a direction vertical to a median line of a pet as shown in FIG. 2.

Figure 5:
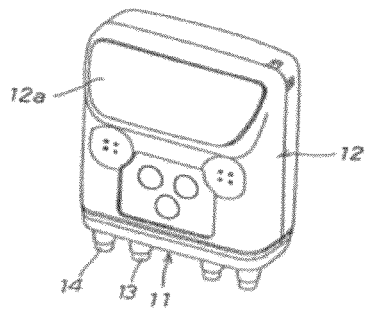
FIG. 5 is a perspective view showing one example of the pet body fat measuring tool according to another embodiment of the present invention.

Moreover, according to an embodiment of the present invention, as shown in FIG. 5, the electrode body 11 and the control calculating section 12 can be integrally fabricated. By configuring as above, the cord to connect the electrode 11 with the control calculating unit 12 is not required and the pet body fat measuring tool can be made compact which enables the measurement by only one operator in any place. Moreover, the control calculating unit 12 preferably has a display section 12a. Also, the integration of the electrode body 11 with the control calculating unit 12 obviates the need of connecting the cord and, therefore, the correction of impedance of the cord is not needed, which enables the accurate measurement of a bioelectrical impedance. No use of the cord is preferable from a viewpoint that measuring accuracy is not adversely affected by a pet's leg being caught by the cord or by the pet being wounded which may lead to the interruption of the measurement.

Hereinafter, the pet body fat measuring tool when being applied to a dog is explained.

Figure 6A:
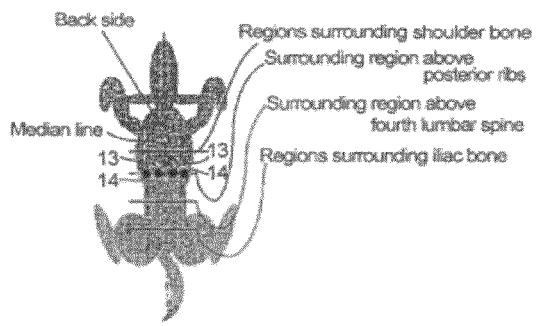
FIG. 6(a) is a diagram explaining the application of the pet body fat measuring tool of the present invention to a dog.
Figure 6B:
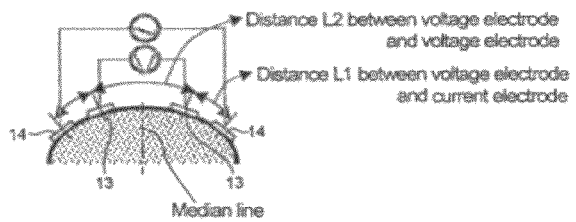
FIG. 6(b) is a diagram explaining the application of the pet body fat measuring tool of the present invention to a dog.

That is, the dog body fat measuring tool 10 of the embodiment of the present invention, as shown in FIGS. 1 and 2, is a body fat measuring unit configured to measure dog body fat by the method of measuring a bioelectrical impedance, in which its electrode body 11 has two voltage electrodes 13 and two current electrodes 14 that are arranged in a straight line so that the distance L1 between the voltage electrode 13 and current electrode 14 is 10 mm and the distance between the voltage electrodes 13 is 30 mm. Moreover, the dog body fat measuring tool 10 is equipped with the control calculating unit 12 having an impedance measuring circuit to control a current made to flow at a time of measurement by being connected to the current electrode 14 and voltage electrode 13 and to calculate body fat based on the bioelectrical impedance determined from measured voltages. The dog body fat measuring tool 10 is used in a manner in which, as shown in FIGS. 6(a) and 6(b), the electrode body 11 is pressed, preferably, to regions surrounding the posterior ribs within a range of a half on a back side of a dog body between the shoulder bone and the iliac bone seen from the body's side.

Figure 6C:
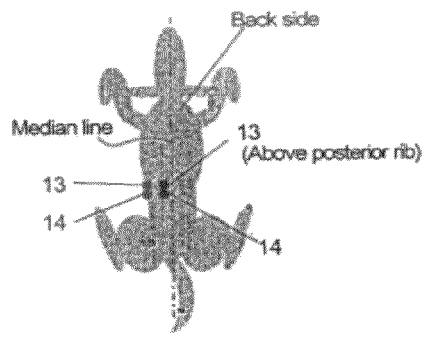
FIG. 6(c) is a diagram explaining the application of the pet body fat measuring tool of the present invention to a dog.
Figure 6D:
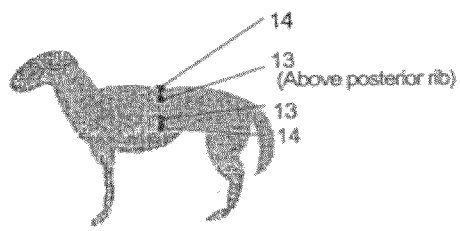
FIG. 6(d) is a diagram explaining the application of the pet body fat measuring tool of the present invention to a dog.

Also, for example, the dog body fat measuring tool 10 can be used in a manner that, as shown in FIG. 6(c), the voltage electrode 13 and voltage electrode 14 aligned in a row are pressed to a region being displaced about 30 mm in parallel to a median line of a back bone and in a manner that, as shown in FIG. 6(d), the voltage electrode 13 and voltage electrode 14 aligned in a row are pressed to a region being vertical to a median line on a back bone. Moreover, when the electrode body 11 having the current electrode 14 and voltage electrode 13 aligned in two rows in a manner to form a square shape is used, the dog body fat measuring tools 10 can be operated in a manner in which, as shown in FIG. 6(d), the electrode body 11 is pressed to one of body sides that sandwich the back bone.

According to the dog body fat measuring tool 10 of the embodiment of the present invention, when the measurement is made by pressing the electrode body 11 to the back of a dog, preferably, an electrolysis solution or organic solvent is held and supported by body hairs existing between a body surface of the dog back and a surface of each of electrodes 13, 14. This makes it possible to measure dog body fat more accurately. Alternatively, by sandwiching an electrolysis solution or organic solvent impregnating body made up of a sponge, woven fabric, unwoven fabric, absorbent cotton, or the like being impregnated with these electrolysis solutions or organic solvents between the body surface of a dog back and each of the electrodes 13, 14, body hairs existing between the body surface of the dog back and each of the electrodes 13, 14 can be made to support the electrolysis solutions or organic solvents.

Moreover, the electrolysis solution or organic solvent impregnating body may or may not be electrically conductive. In the case the conductive electrolysis solution or organic solvent is conductive, a conductive sponge or the like can be used. The use of the electrolysis solution or organic solvent impregnating body by being sandwiched between the surface of a dog body and each of the electrodes 13, 14 is not necessarily required and body hairs can be made to hold and support the electrolysis solution or organic solvent by directly applying the solution or organic solvent to the body hairs. According to the pet body fat measuring tool 10 of the present invention, it is not necessarily required that the electrolysis solution or organic solvent is held and supported by body hairs existing between the surface of a pet body and each of the electrodes 13, 14 and the pet body fat measuring tool 10 can be also used in a manner in which, for example, the surface of each of the electrodes 13, 14 may be pressed to a region where body hairs are shaved. Additionally, the surface of each of the electrodes 13, 14 may be pressed to a region where body hairs are pushed aside. If used at those conditions, to make the electrolysis solution or organic solvent be held and supported by body hairs existing surround the regions where body hairs are pushed aside is preferable in terms of measuring accuracy.

Another method of holding and supporting an electrolysis solution or organic solvent includes a method in which the electrolysis solution or organic solvent is directly supplied to a surface of the electrode body 11 from an electrolysis solution or organic solvent supplying section directly connected to the surface of each of the electrodes 13, 14. That is, when, for example, the electrode body 11 shown in FIG. 2 is used, as shown in FIG. 4(a), a metal thin plate of each of the current electrodes 14 and voltage electrodes 13 arranged, in a protruded manner, on a pressing surface of the electrode body 11 is fabricated to be hemispherical using a pressing process and the electrolysis solution or organic solvent flowing holes 16 are formed in a central portion and the electrolysis solution or organic solvent to be supplied via a supplying tube 17 connected to a base terminal portion of each of the electrodes 13, 14 may be made to be emitted from a tip of each of the electrodes 13, 14 through the electrolysis solution or organic solvent flowing holes 16. Also, for example as shown in FIG. 4(b), each of the electrodes 13, 14 arranged, in a protruded manner, on a pressing surface of the electrode body 11 may be fabricated by using bolt members 18 in which the electrolysis solution or organic solvent flowing holes 16 are formed in its central portion and each of the electrodes 13, 14 made up of the bolt members 18 may be attached to the electrode body 11 via nut members 19 so that an electrolysis solution or organic solvent supplied through supplying tubes 17 connected to a base terminal portion of each of the electrodes 13, 14 is made to be emitted from an end portion of each of the electrodes 13, 14 via the electrolysis solution or organic solvent flowing holes 16.

Furthermore, each of the current electrodes 13 and voltage electrodes 14 of the electrode body 11 is connected to one end of each of connecting codes 15 attached, and inserted into the inside of the electrode body 11, and another end of each of the connecting codes 15 is connected to the control calculating unit 12 having the same configurations as described above through a connector 20 (see FIG. 1) and, therefore, a current made to flow at a time of the measurement is controlled and pet body fat can be easily calculated based on bioelectrical impedance determined from measured voltages.

In order to measure pet body fat by using the pet body fat measuring tool of the present invention, body fat percentage needs to be measured accurately, in advance, according to a deuterium oxide dilution method or the like and a relationship equation between the body fat percentage and impedance value measured by the pet body fat measuring tool of the present invention has to be formed in advance. Thereafter, a body fat percentage can be calculated simply by measuring the impedance value. Additionally, by inputting data on a weight of a pet separately, the body fat amount (weight) can be calculated when a bioelectrical impedance is measured and the result can be immediately displayed on a display section.

EXAMPLES

Hereinafter, the present invention is explained in detail by referring to examples.

Experimental Example 1

Measurements shown below were made on fifteen dogs raised as a pet at homes and brought to animal hospitals.

[Measurement of Body Fat Percentage by Deuterium Oxide Dilution Method]

First, accurate measurement of a body fat percentage on each dog (individual No. 1 to 15) shown in Table 1 was made according to a method by Burkholder et al.[1] However, the measurement was carried out with no anesthetic. Blood (6 ml) was drawn from a cervical vein and a serum separation was performed to use the separated serum as a serum sample before the injection of heavy water. Then, while a pterygoid needle is being retained in a vein of the front leg, 0.2 ml / (kg bodyweight) of heavy water was measured and taken using a syringe and injected and further 10 ml of heparin sodium normal saline solution was injected. A weight of the syringe before and after the injection was measured and the difference between the weight before the injection and weight after the injection was used as an injected amount $(W_{D20})$g of heavy water. As diffusion time of heavy water, 90 minutes were given. Thereafter, 6 ml of blood was again drawn from a cervical vein on an opposite side and a serum separation was performed to use the drawn serum as a serum sample after the injection of heavy water. Concentration of heavy water was analyzed by using an IRMS (Isotope Ratio Mass Spectrometry) method. The concentration in the serum sample before the injection was represented as $(C_1)$ ppm and the concentration in the serum sample after the injection as $(C_2)$ ppm and an amount of the injected heavy water was represented as $(W_{D20})$g. The body weight was represented as (BW) kg and a body fat percentage was calculated by the following calculating equation:

$$\text{Body fat percentage}(\%) = 100 - \{10^5 W_{D20}/(C_2 - C_1)\}/0.732 BW$$

[1]: William J. Burkholder, Craig D. Thatcher AJVR 59(8) 1998 927-937.

[Impedance Measurement by Tool of Present Invention]

The distance L1 between the voltage electrode 13 and the current electrode 14 of the electrode body 11 shown in FIG. 2 was set to be 10 mm and the distance L2 between the voltage electrodes 13 of the electrode body 11 shown in FIG. 2 was set to be 60 mm, and the measurement was made according to the following procedures. First, after a surrounding region above a posterior rib shown in FIG. 6(a) of each of the dogs shown in Table 1 was wiped clean with a solution containing 99.5% by weight of ethanol, a region surrounding the posterior ribs of each of the dogs was applied with a solution containing 0.9% by weight of a physiological saline solution impregnated by an absorbent cotton and then the above electrode body 11 was pressed to the dog body region applied with the physiological saline solution. The control calculating unit 12 and the electrode body 11 were connected by the connecting cord 15 and the control calculating unit 12 was placed on a table to measure the impedance. The current value used for the measurement was 0.5 mA and the frequency for the measurement was 50 kHz. A body fat percentage measured on each dog according to the deuterium oxide dilution method, measured bioelectrical impedance value, correlation coefficient, thickness of subcutaneous fat were shown in Table 1 and the relation between the body fat percentage measured according to the deuterium oxide dilution and the impedance value was shown in FIG. 7 with their correlation coefficients.

Figure 7:
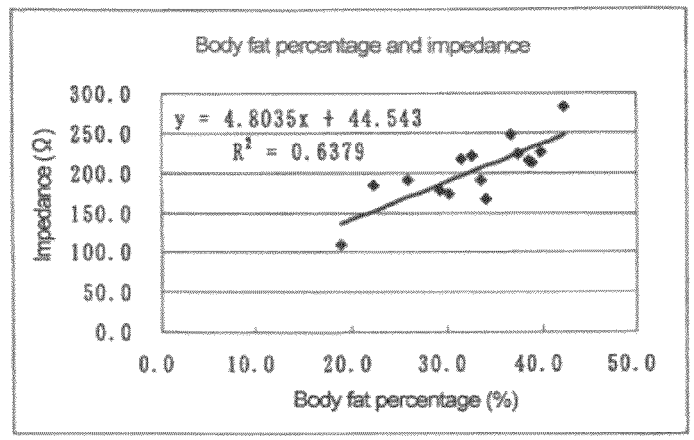
FIG. 7 is a diagram showing the relation between a body fat percentage obtained by using a deuterium oxide dilution method and an impedance measured under conditions in Table 2 by using the pet body fat measuring tool shown in FIG. 1 and FIG. 2.

As shown in FIG. 7, it was found that there is a high correlation between the body fat percentage and impedance obtained by the measurement according to the deuterium oxide dilution method irrespective of the dog kind or body size and, only by the measurement of an impedance, the pet body fat percentage can be measured very easily and accurately.

Experimental Example 2

The measurement of a body fat percentage was made on 9 dogs (all beagle dogs, individual numbers No. 16 to 24) shown in Table 2 according to the deuterium oxide dilution method by the procedures employed in the Experimental Example 1. Also, by using the electrode body 11 shown in FIG. 2 in which the distances shown in Table 3 are used as the distance L1 between the voltage electrode 13 and the current electrode 14 and the distance L2 between the voltage electrodes 13, an impedance was measured by the tool of the present invention by the procedures described in the Experimental Example 1. Correlation coefficients between the measured impedance and the body fat percentage measured according to the deuterium oxide dilution method are shown in Table 3.

TABLE 2

| Individual No. | Dog kind | Body weight (kg) | Trunk length (cm) | Body fat percentage (%) by deuterium oxide dilution method |
|---|---|---|---|---|
| 16 | Beagle | 19.8 | 31 | 33.2 |
| 17 | " | 10.3 | 28 | 11.9 |
| 18 | " | 10.6 | 29 | 14.1 |
| 19 | " | 17.8 | 33 | 35.2 |
| 20 | " | 13.2 | 28 | 31.0 |
| 21 | " | 11.5 | 33 | 9.0 |

TABLE 1

| Individual No. | Dog kind | Body weight (kg) | Trunk length (cm) | Body fat percentage (%) by deuterium oxide dilution method | Bioelectrical impedance (Ω) | Subcutaneous fat thickness (cm) |
|---|---|---|---|---|---|---|
| 1 | Welsh Corgi Pembroke | 14.1 | 39 | 19.0 | 110.2 | 0.8 |
| 2 | Labrador Retriever | 30.2 | 49 | 29.3 | 177.4 | 1.2 |
| 3 | Miniature Dachshund | 9.6 | 37 | 31.5 | 216.7 | 0.8 |
| 4 | Beagle | 9.1 | 34 | 33.5 | 189.6 | 1.05 |
| 5 | Miniature Dachshund | 6.7 | 34 | 34.2 | 165.4 | 0.8 |
| 6 | Miniature Dachshund | 6.6 | 31 | 37.4 | 223.8 | 1.2 |
| 7 | Miniature Dachshund | 6.5 | 34 | 38.6 | 213.6 | 1.6 |
| 8 | Beagle | 15.7 | 37 | 39.0 | 212.3 | 1.1 |
| 9 | Miniature Dachshund | 6.1 | 34 | 39.8 | 225.6 | 0.8 |
| 10 | Cairn Terrier | 7.0 | 30 | 42.3 | 282.0 | 1.6 |
| 11 | Shih Tzu | 7.1 | 34 | 25.9 | 190.0 | 0.9 |
| 12 | Miniature Dachshund | 6.7 | 38 | 30.1 | 172.0 | 1.1 |
| 13 | Chihuahua | 4.1 | 29 | 22.4 | 183.2 | 0.65 |
| 14 | Maltese | 6.5 | 32 | 36.7 | 248.2 | 1.2 |
| 15 | Chihuahua | 3.5 | 29 | 32.6 | 221.8 | 0.8 |

TABLE 2-continued

| Individual No. | Dog kind | Body weight (kg) | Trunk length (cm) | Body fat percentage (%) by deuterium oxide dilution method |
|---|---|---|---|---|
| 22 | " | 12.5 | 32 | 20.0 |
| 23 | " | 12.0 | 32 | 14.6 |
| 24 | " | 12.8 | 32 | 17.1 |

TABLE 3

Unit: Ω

| | | Distance L2 between V and V (mm) | | | | | | | | | | | |
|---|---|---|---|---|---|---|---|---|---|---|---|---|---|
| | | 10 | | | 30 | | | 60 | | | 100 | 200 | 450 |
| | | Distance L1 between V and I (mm) | | | | | | | | | | | |
| | | 8 | 10 | 90 | 4 | 6 | 10 | 8 | 10 | 30 | 90 | 10 | 10 | 10 |
| Individual No. | 16 | 146.8 | 103.2 | 35.0 | 419.5 | 318.6 | 152.6 | 281.8 | 214.8 | 94.8 | 29.7 | 284.4 | 326.0 | 137.2 |
| | 17 | 70.4 | 60.8 | 20.2 | 343.4 | 162.7 | 75.4 | 180.0 | 102.8 | 48.8 | 25.0 | 120.4 | 119.2 | 92.4 |
| | 18 | 87.0 | 63.8 | 24.0 | 316.4 | 188.4 | 103.8 | 149.0 | 125.4 | 43.6 | 23.2 | 162.6 | 174.6 | 93.4 |
| | 19 | 166.2 | 152.4 | — | 465.3 | 282.4 | 210.4 | 335.6 | 269.6 | 94.8 | — | 287.8 | 323.8 | — |
| | 20 | 165.4 | 135.6 | — | 438.5 | 323.1 | 189.2 | 281.0 | 256.0 | 95.6 | — | 261.0 | 337.8 | 154.6 |
| | 21 | 81.4 | 39.0 | 21.6 | 245.9 | 106.6 | 74.4 | 98.0 | 77.6 | 41.6 | 22.4 | 103.2 | 109.8 | — |
| | 22 | 129.0 | 87.6 | — | 464.7 | 164.5 | 108.8 | 179.8 | 134.8 | 61.0 | — | 174.6 | 239.2 | — |
| | 23 | 73.0 | 43.2 | 20.0 | 268.0 | 126.8 | 61.4 | 124.2 | 98.8 | 40.4 | 22.4 | 136.0 | 162.1 | 62.4 |
| | 24 | 93.0 | 71.0 | 19.7 | 314.2 | 175.3 | 113.4 | 174.8 | 140.2 | 46.4 | 22.8 | 165.6 | 216.8 | — |
| Correlation coefficient | | 0.90 | 0.83 | 0.79 | 0.36 | 0.87 | 0.97 | 0.92 | 0.94 | 0.94 | 0.77 | 0.98 | 0.95 | 0.78 |

Distance between V and V: Distance between centers of voltage electrodes: L2
Distance between V and I: Distance between center of voltage electrode and center of current electrode: L1

Irrespective of the distance L1 between the center of the current electrode 14 and the center of the voltage electrode 13, the correlation coefficient between the body fat percentage measured according to the deuterium oxide dilution method and the measured impedance was high, and, in the distance range between 5 mm to 30 mm in particular, the correlation coefficient was much higher. It was also found that, irrespective of the distance L2 between the centers of the voltage electrodes 13, the correlation coefficient between the body fat percentage measured according to the deuterium oxide dilution method and impedance measured by the tool of the present invention is high, and, in the distance range between 10 mm to 100 mm in particular, the correlation coefficient is much higher and the pet body fat percentage can be measured very easily and very accurately. By setting the distances L1 and L2 between the electrodes to be narrow to some extent, the measuring tool can be made compact, thus easily making the measurement with high accuracy.

Experimental Example 3

By setting the distance L1 between the voltage electrode 13 and the current electrode 14 of the electrode body 11 as shown in FIG. 2 to be 10 mm and the distance L2 between the voltage electrodes 13 of the electrode body 11 to be 60 mm, measurement of an impedance was made on each dog shown in Table 2 by using the tool of the present invention according to the procedures described in the Experimental Example 1. The measurement was made on three regions including the surrounding site above the posterior ribs, the surrounding site above the fourth lumber spine, and the surrounding site above the iliac bone as shown in FIG. 6(a). Correlation coefficients between the measured impedance and body fat percentage measured according to the deuterium oxide dilution method in each dog were shown in Table 4.

TABLE 4

Unit: Ω

| Measured region | | Surrounding site above posterior rib | Surrounding site above fourth lumber spine | Surrounding site above iliac bone |
|---|---|---|---|---|
| Individual No. | 16 | 209.2 | 227.0 | 207.8 |
| | 17 | 110.2 | 142.8 | 124.2 |
| | 18 | 124.6 | 153.8 | 148.0 |
| | 19 | 256.2 | 265.8 | 218.6 |
| | 20 | 227.0 | 222.8 | — |

TABLE 4-continued

Unit: Ω

| Measured region | | Surrounding site above posterior rib | Surrounding site above fourth lumber spine | Surrounding site above iliac bone |
|---|---|---|---|---|
| | 21 | 93.8 | 99.6 | 107.6 |
| | 22 | 155.2 | 168.0 | 137.0 |
| | 23 | 135.8 | 148.2 | 120.0 |
| | 24 | 155.2 | 158.2 | 179.6 |
| Correlation coefficient | | 0.91 | 0.97 | 0.95 |

It is also found that, in any region in which the measurement is made, the correlation coefficient between the body fat percentage measured by the deuterium oxide dilution method and the impedance measured by the tool of the present invention is high and the pet body fat percentage can be measured very easily and accurately.

Experimental Example 4

Figure 6E:
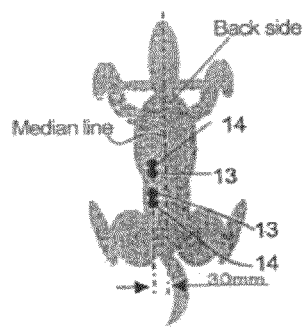
FIG. 6(e) is a diagram explaining the application of the pet body fat measuring tool of the present invention to a dog.

By using the electrode body 11 shown in FIG. 2 (hereinafter, referred to as "electrodes arranged in a straight line" and the electrodes shown in FIG. 3 (hereinafter, referred to as "electrodes arranged in a square shape") and by setting the distance L1 between the voltage electrode 13 and the current electrode 14 of the electrode body 11 to be 10 mm and the distance L2 between the voltage electrodes 13 of the electrode body 11 to be 30 mm, measurement of the impedance was made on the surrounding site above the posterior rib of each dog shown in Table 2 using the tool of the present invention according to the procedure described in the Experimental Example 1. In the case of the electrodes arranged in a straight line, the measurement was made by arranging each of the electrodes 13, 14 of the electrode body 11 in a straight line to the form being in parallel to a median line (longitudinal central line in the top view) and 30 mm apart from the median line [see FIG. 6(c)] and also by arranging each of the electrodes 13, 14 to the form being vertical to the median line and by arranging the current electrode 14 being nearest to the median line at a place 10 mm apart from the median line [see FIG. 6(d)]. Also, in the case of the electrodes arranged in a square shape, the measurement was made by arranging a pair of the current electrode 14 and voltage electrode 13 nearest to the median line arranged to the form being 10 mm from the median line [see FIG. 6(e)]. A correlation coefficient between the measured impedance and the body fat percentage measured according to the deuterium oxide dilution method in each dog is shown in Table 5.

TABLE 5

| Arrangement of electrode body | | | Unit: Ω |
|---|---|---|---|
| | ① | ② | ③ |
| Individual No. 16 | — | — | 221.8 |
| 17 | 72.2 | 93.0 | 106.3 |
| 18 | 108.8 | — | 109.2 |
| 19 | 208.0 | 224.4 | 244.3 |
| 20 | 169.4 | 222.8 | 242.1 |
| 21 | — | — | 76.9 |
| 22 | 84.6 | 138.4 | 125.7 |
| 23 | 75.6 | 96.6 | 95.3 |
| 24 | 88.2 | 136.0 | 147.8 |
| Correlation coefficient | 0.94 | 0.97 | 0.95 |

It was also found that there is no difference in results from the measurements among any arrangements of the electrodes 13, 14 and among any methods of application of the electrodes 13, 14. In addition, it was found that the correlation coefficient between the body fat percentage measured by the deuterium oxide dilution method and the impedance measured by the tool of the present invention is high and the pet body fat percentage can be measured very easily and accurately.

Experimental Example 5

By using the pet body fat measuring tool shown in FIG. 5 and by setting the distance between the voltage electrode 13 of the electrode body 11 and the current electrode 14 of the electrode body 11 to be 15 mm and the distance between the voltage electrodes 13 of the electrode body 11 to be 30 mm, measurement of an impedance was made on the surrounding site above the posterior ribs of each dog shown in Table 6 by the following procedures. First, a surrounding portion of a left half body region of each dog on the posterior rib side being in parallel to a median line of the dog and 20 mm in distance from the median line was wiped clean with a solution containing about 75% by weight of ethanol (ethanol for disinfection manufactured by WAKO CHEMICAL, LTD.) and hairs of each dog were pushed aside linearly. After that, by pressing an absorbent cotton containing about 75% by weight of ethanol on a whole region in which the hairs were pushed aside, hairs and skin were applied with ethanol and, before the evaporation of ethanol, the electrode was pressed to the region applied with ethanol to measure the impedance. At that time, the current value was about 0.2 mA and the frequency was 50 kHz. The correlation diagram between the body fat percentage of each dog by the deuterium oxide dilution method and the measured impedance is shown in FIG. 9.

TABLE 6

| Individual No. | Dog kind | Body fat percentage (%) by deuterium oxide dilution method | Bioelectrical impedance (Ω) |
|---|---|---|---|
| 25 | Pomeranian | 18.2 | 93.5 |
| 26 | Maltese | 16.9 | 105.2 |
| 27 | Golden Retriever | 27.0 | 105.4 |
| 28 | Alaskan Malamute | 23.9 | 171.0 |
| 29 | Basset Hound | 36.1 | 194.2 |
| 30 | Cavalier King Charles Spaniel | 26.0 | 143.1 |
| 31 | Miniature Schnauzer | 24.5 | 109.1 |
| 32 | Papillon | 19.0 | 97.8 |
| 33 | Chihuahua | 28.6 | 188.5 |
| 34 | Miniature Dachshund | 16.8 | 103.4 |
| 35 | Miniature Dachshund | 35.4 | 166.8 |
| 36 | Yorkshire Terrier | 24.1 | 147.3 |
| 37 | Chihuahua | 33.4 | 213.6 |
| 38 | Chihuahua | 39.7 | 236.3 |
| 39 | Miniature Dachshund | 31.6 | 136.2 |
| 40 | Welsh Corgi Pembroke | 42.1 | 230.0 |
| 41 | Shih Tzu | 39.4 | 212.6 |
| 42 | Miniature Dachshund | 30.0 | 131.4 |
| Correlation coefficient | | 0.86 | |

Figure 9:
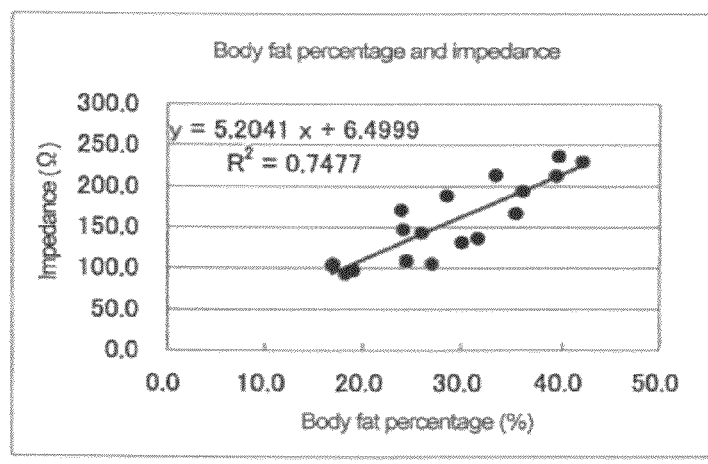
FIG. 9 is a diagram showing the relation between thickness of body fat obtained by using the deuterium oxide dilution method and impedance value obtained by measurement in each dog shown in Table 6 using the pet body fat measuring tool shown in FIG. 5.

As shown in FIG. 9, it was also found that, even when an organic solvent not containing an electrolyte, instead of an electrolysis solution, is used for the measurement, the correlation coefficient between the body fat percentage measured by the deuterium oxide dilution method and the impedance measured by the tool of the present invention is high ($R^2=0.75$) and the pet body fat percentage can be measured very easily and accurately.

Reference Example 1

Measurements of a thickness of subcutaneous fat in a surrounding site above the posterior ribs were made on each dog shown in Table 1 by using an X-ray tomography method. The relation between a body fat percentage of each dog measured according to the deuterium oxide dilution method and a thickness of subcutaneous fat, the relation between the impedance measured on the surrounding site above the posterior ribs by using the tool of the present invention and the thickness of subcutaneous fat, and correlation coefficients among them are shown in FIGS. 8(a) and 8(b).

Figure 8A:
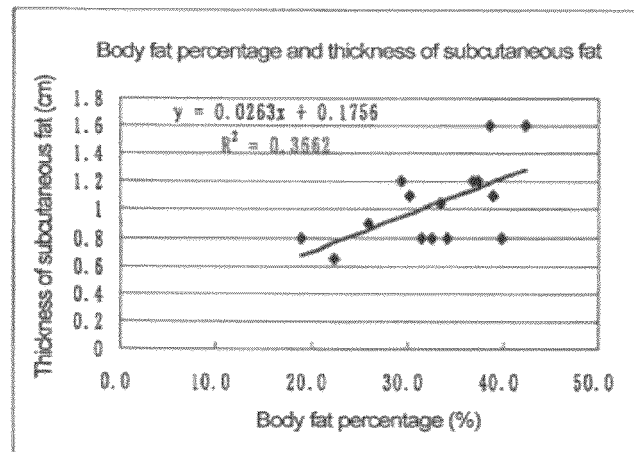
FIG. 8(a) is a diagram showing the relation between a body fat percentage obtained by using the deuterium oxide dilution method and thickness of subcutaneous fat obtained by X-ray tomography.
Figure 8B:
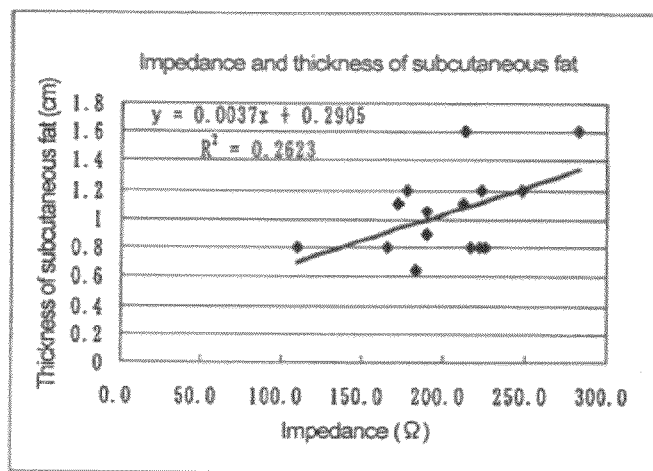
FIG. 8(b) is a diagram showing the relation between a thickness of subcutaneous fat obtained by X-ray tomography and measured impedance value obtained by using the pet body fat measuring tool of the present invention.

In each dog shown in Table 1 which is used for the present experimental examples, as shown in FIGS. 8(a) and 8(b), simple measurement of a thickness of subcutaneous fat was insufficient for measurement of the body fat percentage. This is because there is a big difference in every physical status of a dog and, even if the body fat percentage is the same, an absolute thickness of subcutaneous fat is different in every dog.

Industrial Applicability

By applying the pet body fat measuring tool and the pet body fat measuring method of the present invention, body fat of a small-sized pet animal such as a dog, cat, or the like can be measured based on the impedance method very easily and accurately.

The invention claimed is:

1. A pet body fat measuring tool for measuring pet body fat by measuring a bioelectrical impedance comprising:
    an electrode body including two current electrodes and two voltage electrodes, and the electrode body is configured to be pressed to a part of a pet body;
    a control calculating unit having an impedance measuring circuit connected to the electrode body to control a current made to flow at a time of measurement, wherein the control calculating unit stores, in advance of the measurement, a direct correlation between a body fat percentage of a pet body and the bioelectrical impedance of the pet body so as to calculate the body fat percentage based on only a bioelectrical impedance determined from a measured voltage; and one or more protrusions arranged in portions separated from and surrounding each of the electrodes, wherein a distance between each of the current electrodes and each of the voltage electrodes of the electrode body is fixed.

2. The pet body fat measuring tool according to claim 1, wherein a distance between a center of a first one of the voltage electrodes and a center of a closest one of the current electrodes to the first one of the voltage electrodes is 5 mm to 30 mm, and a distance between a center of a second one of the voltage electrodes and a center of a closest one of the current electrodes to the second one of the voltage electrodes is 5 mm to 30 mm.

3. The pet body fat measuring tool according to claim 1, wherein a distance between centers of the two voltage electrodes is 10 mm to 300 mm.

4. The pet body fat measuring tool according to claim 1, wherein one or more protrusions are arranged in portions separated from and surrounding each of the electrodes with intervals of 0.5 mm to 10 mm between each of the protrusions and a closest one of the electrodes.

5. The pet body fat measuring tool according to claim 4, wherein a height of each of the protrusions arranged in portions separated from and surrounding each of the electrodes is less than a height of each of the electrodes, and a difference in height between each of the protrusions and each of the electrodes is within 5 mm.

6. The pet body fat measuring tool according to claim 4, wherein a section of each of the protrusions is elliptical, or rectangular, or a combination thereof with a long side of the section being 1 mm to 5 mm and with a short side of the section being 1 mm to 3 mm.

7. The pet body fat measuring tool according to claim 1, wherein the electrode body and the control calculating unit are integrally fabricated.

8. The pet body fat measuring tool according to claim 1, wherein each of the electrodes and the protrusions are arranged in a straight line.

9. The pet body fat measuring tool according to claim 8, wherein two of the protrusions positioned in the straight line are positioned outside an area extending between the two current electrodes.

10. The pet body fat measuring tool according to claim 1, wherein a distance between the two voltage electrodes is smaller than a distance between the two current electrodes.

11. The pet body fat measuring tool according to claim 1, wherein at least two of the protrusions are positioned between a first one of the two current electrodes and a closest one of the two voltage electrodes, and at least another two of the protrusions are positioned between a second one of the two current electrodes and a closest one of the two voltage electrodes.

12. A dog body fat measuring method, comprising:
pressing an electrode body including two current electrodes and two voltage electrodes to a part of a dog body,
flowing a current between the two current electrodes,
measuring a voltage between the two voltage electrodes, and
calculating a body fat percentage from a direct correlation between body fat percentage and bioelectrical impedance of a dog body, based only on the bioelectrical impedance determined from the measured voltage, wherein
a distance between each of the current electrodes and each of the voltage electrodes of the electrode body is fixed, and
the part of the dog body to which the electrode body is pressed is on a back side of the dog body and between a shoulder bone of the dog body and an iliac bone of the dog body.

13. The dog body fat measuring method according to claim 12, further comprising:
distributing an electrolysis solution or organic solvent between a surface of the dog body with body hairs and a surface of each of the electrodes.

14. The dog body fat measuring method according to claim 12, wherein each of the electrodes and at least two protrusions that surround each of the electrodes are arranged in a straight line.

15. The dog body fat measuring method according to claim 12, further comprising:
determining the direct relationship by measuring the body fat percentage of the direct relationship using a deuterium oxide dilution method, and calculating an equation between the measured body fat percentage and the bioelectrical impedance of the direct relationship.

* * * * *